United States Patent
Sekiya et al.

(10) Patent No.: US 10,175,204 B2
(45) Date of Patent: Jan. 8, 2019

(54) METHOD OF SORTING CHIPS

(71) Applicant: DISCO CORPORATION, Tokyo (JP)

(72) Inventors: Kazuma Sekiya, Tokyo (JP); Hiroshi Morikazu, Tokyo (JP)

(73) Assignee: Disco Corporation, Tokyo (JP)

( * ) Notice: Subject to any disclaimer, the term of this patent is extended or adjusted under 35 U.S.C. 154(b) by 0 days.

(21) Appl. No.: 15/585,937

(22) Filed: May 3, 2017

(65) Prior Publication Data

US 2017/0328867 A1    Nov. 16, 2017

(30) Foreign Application Priority Data

May 10, 2016   (JP) ................................ 2016-094301

(51) Int. Cl.
| | |
|---|---|
| *G01N 29/04* | (2006.01) |
| *B07C 5/342* | (2006.01) |
| *G01N 29/22* | (2006.01) |
| *H03H 3/08* | (2006.01) |
| *G01N 29/12* | (2006.01) |
| *G01N 29/44* | (2006.01) |

(52) U.S. Cl.
CPC ......... *G01N 29/043* (2013.01); *B07C 5/3422* (2013.01); *G01N 29/045* (2013.01); *G01N 29/12* (2013.01); *G01N 29/223* (2013.01); *G01N 29/4445* (2013.01); *H03H 3/08* (2013.01); *G01N 2291/014* (2013.01); *G01N 2291/0258* (2013.01); *G01N 2291/0289* (2013.01)

(58) Field of Classification Search
CPC . B07C 5/34; B07C 5/3422; B07C 2501/0027; G01N 3/00; G01N 29/00; G01N 29/04; G01N 29/14; G01N 29/34; G01N 29/043; G01N 2291/0258; G01N 2291/0289
USPC .................... 209/552, 590, 599, 699
See application file for complete search history.

(56) References Cited

U.S. PATENT DOCUMENTS

| | | | |
|---|---|---|---|
| 2005/0092089 A1* | 5/2005 | Gilgunn ................. | G01N 29/14 73/587 |
| 2010/0039128 A1* | 2/2010 | Nitsch .................... | G01N 29/14 324/762.05 |
| 2012/0153444 A1* | 6/2012 | Haga ................... | H01L 23/4334 257/666 |
| 2014/0208850 A1* | 7/2014 | Kim ....................... | G01N 29/14 73/587 |

(Continued)

FOREIGN PATENT DOCUMENTS

JP    2013-065997    4/2013

*Primary Examiner* — Joseph C Rodriguez
*Assistant Examiner* — Kalyanavenkateshware Kumar
(74) *Attorney, Agent, or Firm* — Greer Burns & Crain Ltd.

(57) ABSTRACT

A method of sorting chips divided from a plate-shaped workpiece into acceptable chips and defective chips includes an ultrasonic vibration applying step of applying ultrasonic vibrations to chips, a fracture confirming step of confirming whether the chips have been fractured in the ultrasonic vibration applying step or not, and a sorting step of sorting those chips which have been confirmed as not fractured in the fracture confirming step as acceptable chips. The ultrasonic vibrations applied to the chips in the ultrasonic vibration applying step are set to values that do not cause chips to be fractured if the chips are free of minute fractures and cause chips to be fractured if the chips contain minute fractures.

2 Claims, 5 Drawing Sheets

(56) References Cited

U.S. PATENT DOCUMENTS

2015/0200181 A1\* 7/2015 Haga .................. B23K 20/005
438/127

\* cited by examiner

METHOD OF SORTING CHIPS

BACKGROUND OF THE INVENTION

Field of the Invention

The present invention relates to a method of sorting chips into acceptable chips and defective chips.

Description of the Related Art

For manufacturing surface acoustic wave (SAW) devices, for example, it has been customary to form a plurality of SAW elements on a wafer of lithium tantalate (LT) as a plate-shaped workpiece, then divide the wafer into a plurality of SAW chips using a dicing apparatus or a laser processing apparatus, and thereafter package the SAW chips, thereby producing SAW devices.

The SAW chips divided from the wafer are likely to suffer fractures such as minute breaks, cracks, etc. caused when they are divided. The SAW devices which contain such fractures are not only unable to give their desired performance, but also liable to deteriorate or fracture themselves even when used under standard conditions. Therefore, it has been the practice in the art to carry out an appearance inspection to check whether chips to be packaged have been fractured or not and then package only those chips that have been found acceptable in the appearance inspection, or to perform a sampling test, such as a reliability test including a thermal cycle test, an impact test, or the like, on packaged devices.

SUMMARY OF THE INVENTION

One problem with the conventional approach is that if a fracture is minute or occurs inside a SAW element or a chip, then it is difficult to detect in the appearance inspection. Consequently, a defective device containing a fracture may not be judged as being defective in the appearance inspection, but may be shipped out of a factory as an acceptable device. Such a device may fail to give its desired performance, or may tend to deteriorate or fracture itself during usage under standard conditions.

Depending on the type of a reliability test carried out on a chip, the chip may be fractured by the reliability test, or may remain damaged by the reliability test even though it is not fractured. Therefore, it is desirable not to sort the chip as an acceptable chip. Stated otherwise, a certain type of reliability test cannot be performed on all the chips, and the chips that have not undergone the reliability test may possibly turn out to be defective chips.

It is an object of the present invention to provide a method of sorting chips in a manner to reduce the possibility that defective devices fabricated from defective chips will be shipped out of a factory.

In accordance with an aspect of the present invention, there is provided a method of sorting chips divided from a plate-shaped workpiece into acceptable chips and defective chips, including an ultrasonic vibration applying step of applying ultrasonic vibrations to chips, a fracture confirming step of confirming whether the chips have been fractured in the ultrasonic vibration applying step or not, and a sorting step of sorting those chips which have been confirmed as not fractured in the fracture confirming step as acceptable chips, wherein the ultrasonic vibrations applied to the chips in the ultrasonic vibration applying step are set to values that do not cause chips to be fractured if the chips are free of minute fractures and cause chips to be fractured if the chips contain minute fractures.

Preferably, the ultrasonic vibrations applied to the chips in the ultrasonic vibration applying step are set to values that cause chips to be heated to a temperature for not fracturing the chips if the chips are free of minute fractures.

In the method of sorting chips according to the present invention, those chips which contain minute fractures are fractured in the ultrasonic vibration applying step. Therefore, the possibility that chips that are sorted as acceptable chips fail to give their desired performance, and that devices fabricated from chips are liable to deteriorate or fracture themselves under standard conditions is reduced. Consequently, defective devices fabricated from defective chips are less likely to be shipped out of a factory.

Preferably, the chips are heated by the ultrasonic vibrations as well as subjected to physical impact in the ultrasonic vibration applying step. Accordingly, the chips undergo a plurality of types of loads at the time of the ultrasonic vibration applying step. Therefore, the possibility that chips that are sorted as acceptable chips fail to give their desired performance, and that devices fabricated from chips are liable to deteriorate or fracture themselves under standard conditions is further reduced.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

Figure 1:
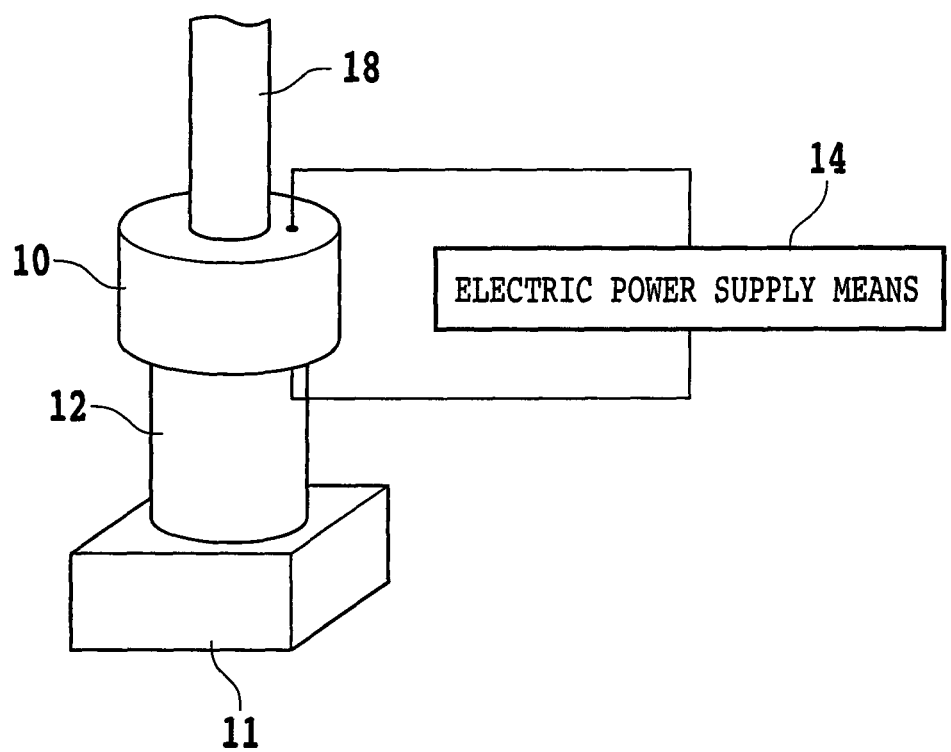
FIG. 1 is a schematic perspective view showing an arrangement for carrying out an ultrasonic vibration applying step.

A method of sorting chips according to a preferred embodiment of the present invention will be described in detail below with reference to the drawings. FIG. 1 shows in schematic perspective an arrangement for carrying out an ultrasonic vibration applying step. In FIG. 1, a chip 11 includes a SAW chip which is fabricated as follows: a plurality of SAW elements are formed on a wafer of LT, and then the wafer is divided into a plurality of SAW chips using a dicing apparatus or a laser processing apparatus. The chip 11 is not limited to a bare chip, but may be a packaged chip.

An ultrasonic vibrator 10 is made of piezoelectric ceramics such as lead zirconate titanate (PZT), barium titanate, lead titanate or the like, or includes a crystal oscillator. The ultrasonic vibrator 10 is supported on a piston rod 18 of an air cylinder, not shown, and a vibration transmitting member 12 is coupled to the distal end of the ultrasonic vibrator 10. For applying ultrasonic vibrations from the ultrasonic vibrator 10 to the chip 11, the air cylinder is actuated to extend the piston rod 18, bringing the vibration transmitting member 12 into contact with the chip 11. Then, electric power supplying means 14 is energized to enable the ultrasonic vibrator 10 to generate ultrasonic waves at a predetermined frequency and a predetermined amplitude.

The ultrasonic waves are transmitted through the vibration transmitting member 12 to the chip 11, which vibrates at a predetermined frequency and a predetermined amplitude. The oscillating frequency of the ultrasonic vibrator 10 varies appropriately depending on the material, size, and thickness of the chip 11, and is set to such a value that the chip 11 will not be fractured if it does not contain minute fractures. If the chip 11 is an LT chip such as a SAW chip having dimensions of 3×3×0.15 (thickness)mm, for example, then the electric power supply means 14 supplies the ultrasonic vibrator 10 with alternating current (AC) electric power having a power level in the range of 10 to 15 W and a frequency in the range of 20 to 40 kHz, preferably from 25 to 30 kHz, enabling the ultrasonic vibrator 10 to ultrasonically vibrate at an amplitude in the range of 10 to 20 µm. The AC electric power which is of the above power level and frequency does not cause the chip 11 to be fractured by ultrasonic vibrations if it is free of minute fractures therein, but causes the chip 11 to be fractured by ultrasonic vibrations if it contains minute fractures therein.

Figure 2:
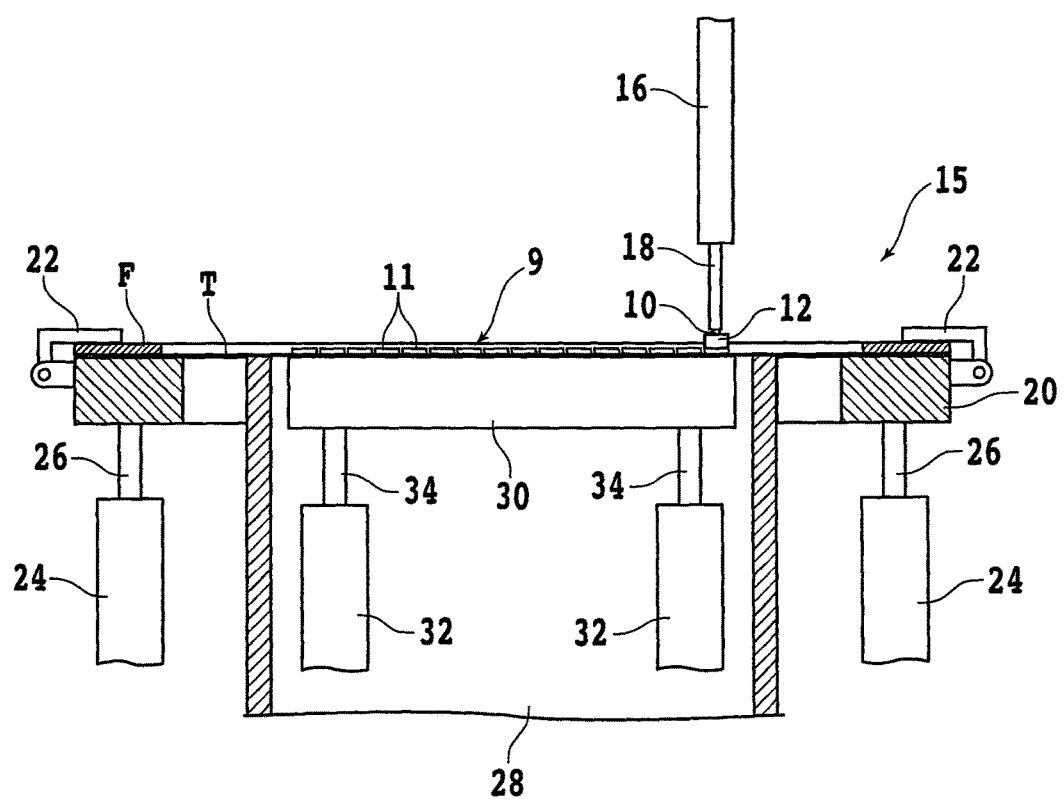
FIG. 2 is a cross-sectional view showing an arrangement for carrying out an ultrasonic vibration applying step in which ultrasonic vibrations are applied to each chip.

An ultrasonic vibration applying step in which ultrasonic vibrations are applied to each chip will be described below with reference to FIG. 2. FIG. 2 shows in cross section an arrangement for carrying out an ultrasonic vibration applying step in which ultrasonic vibrations are applied to each chip. The chip 11 includes, for example, an LT chip divided from an LT wafer 9. The LT wafer 9 has its reverse side adhering to a dicing tape T, which includes an adhesive tape having an outer peripheral edge portion adhering to an annular frame F. After the LT wafer 9 has been processed by a laser processing apparatus, for example, to form laser-processed grooves or modified layers therein along projected dicing lines on the LT wafer 9, the annular frame F is set on an annular support 20 of an expanding apparatus 15, and clamped securely in position on the annular support 20 by a plurality of clamps 22.

The annular support 20 is coupled to the upper ends of piston rods 26 of respective air cylinders 24. The expanding apparatus 15 has an expanding drum 28 having an inside diameter larger than the diameter of the LT wafer 9 adhering to the dicing tape T. The annular frame F is placed on the annular support 20 such that the dicing tape T is held in contact with the upper end of the expanding drum 28. Then, the air cylinders 24 are actuated to retract their piston rods 26 downwardly, moving the annular support 20 coupled to the piston rods 26 downwardly. The dicing tape T is expanded radially outwardly while in abutment against the upper end of the expanding drum 28.

As a result, the LT wafer 9 adhering to the dicing tape T is subjected to radially outward tensile forces. Under the radially outward tensile forces thus applied to the LT wafer 9, the LT wafer 9 is expanded radially outwardly and divided into individual LT chips 11 along the projected dicing lines from the laser-processed grooves or modified layers along projected dicing lines, which serve as division starting points. FIG. 2 illustrates the LT wafer 9 as it has been divided into the LT chips 11 by the expanding apparatus 15. The expanding drum 28 houses therein a support plate 30, preferably made of a hard material, for supporting the LT chips 11 from below through the dicing tape T at the time ultrasonic vibrations are applied to the LT chips 11.

The support plate 30 is coupled to the upper ends of piston rods 34 of respective air cylinders 32. When the LT wafer 9 is divided into the individual LT chips 11 by the expanding apparatus 15, the support plate 30 has been withdrawn to a low position out of contact with the dicing tape T by the air cylinders 32. For applying ultrasonic vibrations to the LT chips 11, the support plate 30 is lifted by the air cylinders 32 to a support position in which the support plate 30 supports the LT chips 11 from below through the dicing tape T. Then, an air cylinder 16 is actuated to lower the vibration transmitting member 12 coupled to the ultrasonic vibrator 10 into contact with one of the LT chips 11. The electric power supply means 14 supplies the ultrasonic vibrator 10 with AC electric power having a power level of 10 W and a frequency of 25 kHz, enabling the ultrasonic vibrator 10 to ultrasonically vibrate at an amplitude in the range of 10 to 20 µm. The ultrasonic vibrations of the ultrasonic vibrator 10 are transmitted through the vibration transmitting member 12 to the LT chip 11, which is ultrasonically vibrated at an amplitude in the range of 10 to 20 µm.

The ultrasonic vibrations that are applied from the ultrasonic vibrator 10 to the LT chip 11 are set to frequency and amplitude values that do not cause the LT chip 11 to be fractured by ultrasonic vibrations if it is free of minute fractures therein, but cause the LT chip 11 to be fractured by ultrasonic vibrations if it contains minute fractures therein. According to the present embodiment, the ultrasonic vibrations are set to a frequency of 25 kHz and an amplitude in the range of 10 to 20 µm. When the application of the ultrasonic vibrations to one LT chip 11 is finished, the air cylinder 16 is moved laterally and the vibration transmitting member 12 is brought into contact with an adjacent LT chip 11. Then, the ultrasonic vibration applying step is carried out on the adjacent LT chip 11. The vibration transmitting member 12 may be of a larger size so that it can simultaneously apply ultrasonic waves to a plurality of LT chips 11.

Under certain conditions, the ultrasonic vibrator 10 is heated at the same time that it generates ultrasonic vibrations. For example, when the ultrasonic vibrator 10 is supplied with AC electric power at a power level of 20 W and a frequency of 25 kHz, the ultrasonic vibrator 10 is heated while being vibrated at an amplitude in the range of 30 to 40 µm. The heat of the ultrasonic vibrator 10 is supplied through the vibration transmitting member 12 to the LT chip 11. Therefore, the physical impact of the ultrasonic vibrations and the heat are simultaneously applied to the LT chip 11, causing the LT chip 11 to be fractured if it contains minute fractures therein, but not causing the LT chip 11 to be fractured if it does not contain minute fractures therein.

Figure 3:
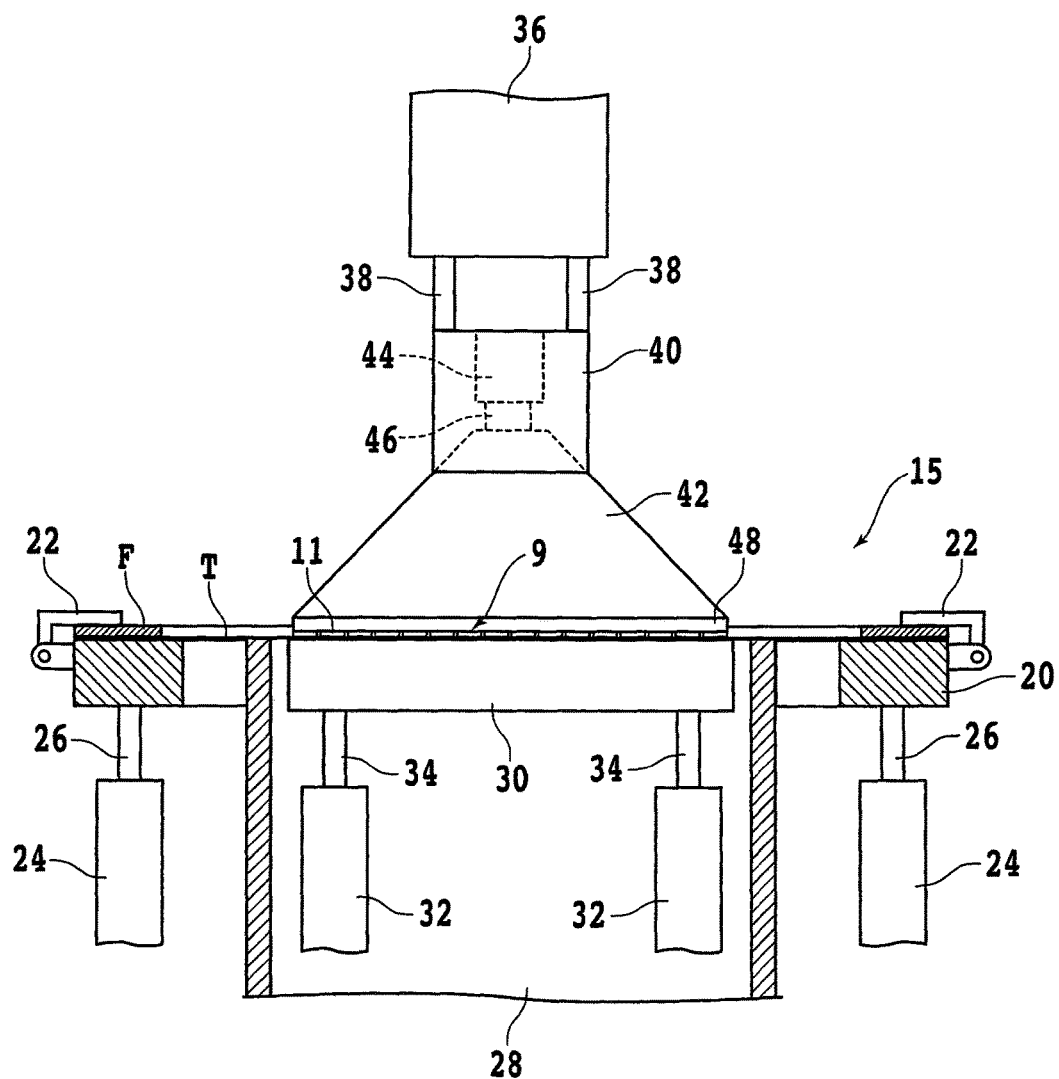
FIG. 3 is a cross-sectional view showing an arrangement for carrying out an ultrasonic vibration applying step in which ultrasonic vibrations are applied to a wafer in its entirety.

FIG. 3 shows in cross section an arrangement for carrying out an ultrasonic vibration applying step in which ultrasonic vibrations are applied to the LT wafer 9 in its entirety. The arrangement shown in FIG. 3 has an ultrasonic vibration applying apparatus 35 including a conical horn 42 having a larger lower distal end whose diameter is substantially the same as the diameter of the LT wafer 9, a support 40 supporting the horn 42, an ultrasonic vibrator 44 disposed in the support 40, a vibration transmitting member 46 disposed between the ultrasonic vibrator 44 and the smaller upper proximal end of the horn 42, and a vibration transmitting member 48 fixed to the lower distal end of the horn 42. The ultrasonic vibration applying apparatus 35 also includes an air cylinder 36 having piston rods 38 whose lower ends are coupled to the support 40.

The arrangement shown in FIG. 3 further has an expanding apparatus 15 which is structurally and operationally identical to the expanding apparatus 15 shown in FIG. 2. Therefore, details of the expanding apparatus 15 will not be described below. In the ultrasonic vibration applying step illustrated in FIG. 3, the air cylinder 36 is actuated to bring the vibration transmitting member 48 fixed to the lower distal end of the horn 42 into contact with the entire LT wafer 9, which has been divided into individual LT chips 11. The electric power supply means, not shown in FIG. 3, supplies the ultrasonic vibrator 44 with AC electric power having a predetermined power level and a predetermined frequency, enabling the ultrasonic vibrator 44 to ultrasonically vibrate at a predetermined frequency and a predetermined amplitude. The predetermined frequency and the predetermined amplitude are set to values similar to those described above with reference to FIG. 2.

Since all the LT chips 11 divided from the LT wafer 9 are covered with the larger lower distal end of the horn 42, the ultrasonic vibrations of the ultrasonic vibrator 44 at the predetermined frequency and the predetermined amplitude are transmitted through the vibration transmitting member 48 simultaneously to all the LT chips 11, which are ultrasonically vibrated under approximately the same conditions. The frequency and amplitude of the ultrasonic vibrations of the LT chips 11 are set to values that do not cause the LT chips 11 to be fractured by ultrasonic vibrations if they are free of minute fractures therein, but cause the LT chips 11 to be fractured by ultrasonic vibrations if they contain minute fractures therein.

As is the case with the arrangement described above with reference to FIG. 2, the AC electric power applied to the ultrasonic vibrator 44 may be set to values that cause the LT chips 11 to be ultrasonically vibrated and heated at the same time. For example, when the electric power supply means supplies the ultrasonic vibrator 44 with AC electric power at a power level of 20 W and a frequency of 25 kHz, the ultrasonic vibrator 44 is heated while being vibrated at an amplitude in the range of approximately 30 to 40 μm. The ultrasonic vibrations and heat of the ultrasonic vibrator 44 is supplied through the vibration transmitting member 46, the horn 42, and the vibration transmitting member 48 to the LT chips 11, which are ultrasonically vibrated and heated.

When the LT chips 11 are thus ultrasonically vibrated and heated, they are fractured if they contain minute fractures therein, but are not fractured if they are free of, minute fractures. If the LT chips 11 are to be heated as well as ultrasonically vibrated, then the support plate 30 should preferably be made of rubber or the like, rather than a hard material.

Figure 4:
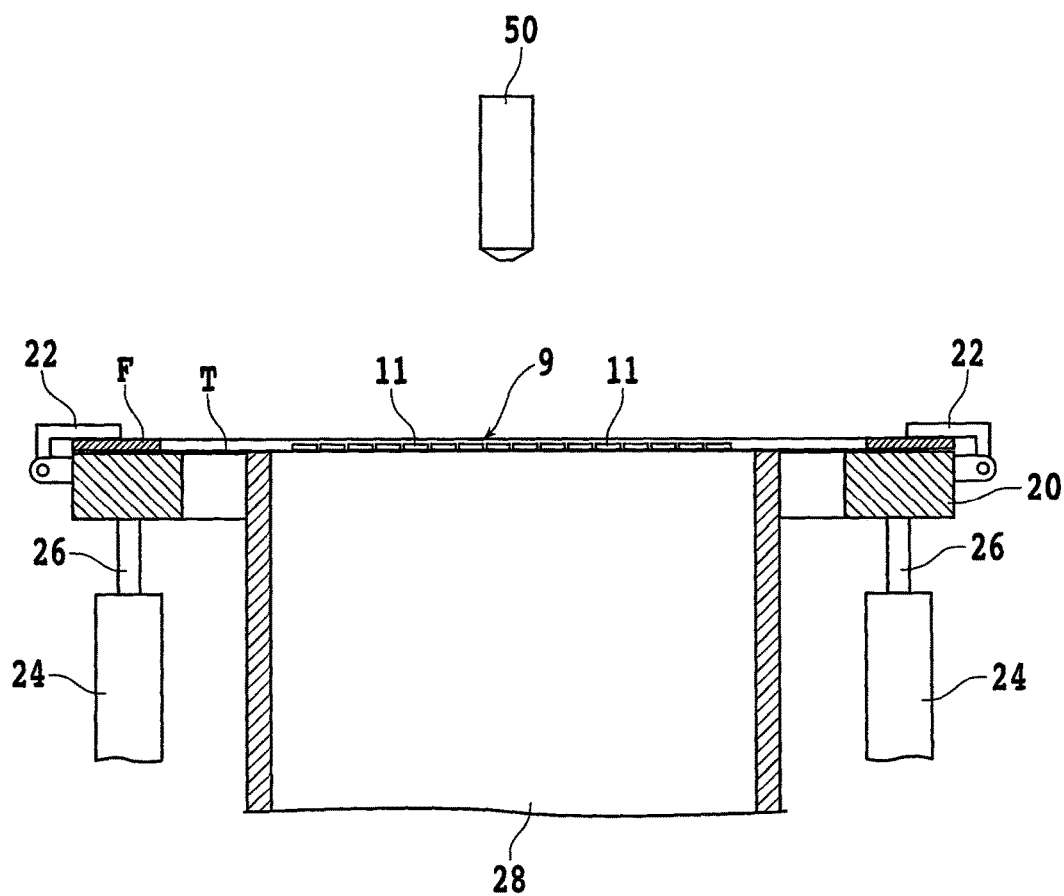
FIG. 4 is a cross-sectional view showing an arrangement for carrying out a fracture confirming step.

After the ultrasonic vibration applying step has been carried out, a fracture confirming step is carried out to confirm whether the LT chips 11 have been fractured by the ultrasonic vibrations or not. In the fracture confirming step, as shown in FIG. 4, each of the LT chips 11 is imaged by an imaging unit 50 including a microscope and a camera, and the captured image is inspected to confirm whether the LT chip 11 has been fractured or not. Alternatively, each of the LT chips 11 may be visually examined through eye observation to confirm whether it has been fractured or not, or a continuity test may be performed on each of the LT chips 11 to confirm whether it has been fractured or not.

Figure 5:
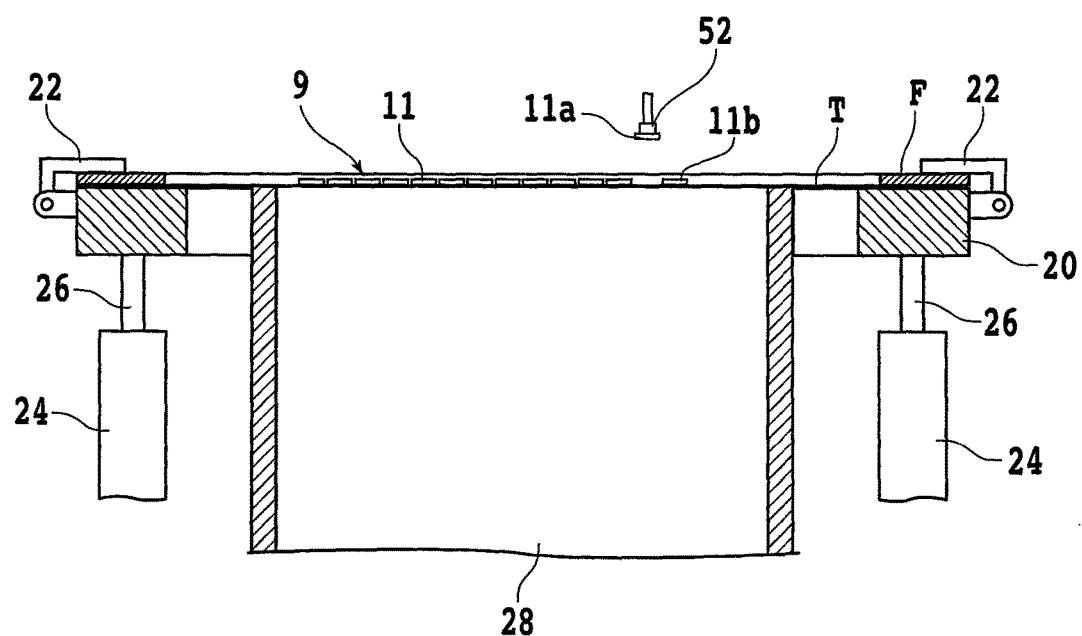
FIG. 5 is a cross-sectional view showing an arrangement for carrying out a sorting step.

The fracture confirming step is followed by a sorting step in which those LT chips 11 that have been confirmed as not fractured in the fracture confirming step are sorted as acceptable chips. In the sorting step, as shown in FIG. 5, only acceptable LT chips 11a are picked up by a pickup collet 52 and delivered to a next step, whereas defective LT chips 11b are left to adhere to the dicing tape T.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A method of sorting chips divided from a plate-shaped workpiece into acceptable chips and defective chips, comprising:
   an ultrasonic vibration applying step of applying ultrasonic vibrations to chips to identify chips that have minute fractures, wherein the ultrasonic vibrations applied to the chips are set to values that do not cause chips to be fractured if the chips are free of minute fractures and cause chips to be further fractured if the chips contain minute fractures;
   a fracture confirming step of confirming whether the chips have been further fractured in the ultrasonic vibration applying step or not; and
   a sorting step of sorting those chips which have been confirmed as not fractured in the fracture confirming step as acceptable chips.

2. The method of sorting chips according to claim 1, wherein the ultrasonic vibrations applied to the chips in the ultrasonic vibration applying step are set to values that cause chips to be heated to a temperature for not fracturing the chips if the chips are free of minute fractures.

\* \* \* \* \*